(12) United States Patent
Jan et al.

(10) Patent No.: US 9,795,347 B2
(45) Date of Patent: Oct. 24, 2017

(54) SCANNING SYSTEM FOR THREE-DIMENSIONAL IMAGING

(71) Applicant: Institute of Nuclear Energy Research Atomic Energy Council, Executive Yuan, Taoyuan County (TW)

(72) Inventors: Meei-Ling Jan, Taoyuan County (TW); Sheng-Pin Tseng, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

(*) Notice: Subject to any disclaimer, the term of this patent is extended or adjusted under 35 U.S.C. 154(b) by 131 days.

(21) Appl. No.: 14/521,770

(22) Filed: Oct. 23, 2014

(65) Prior Publication Data

US 2015/0117597 A1 Apr. 30, 2015

Related U.S. Application Data

(60) Provisional application No. 61/894,979, filed on Oct. 24, 2013.

(30) Foreign Application Priority Data

Oct. 7, 2014 (TW) .............................. 103134914 A

(51) Int. Cl.
| | | |
|---|---|---|
| *A61B 6/00* | (2006.01) | |
| *A61B 6/02* | (2006.01) | |
| *A61B 6/03* | (2006.01) | |
| *A61B 6/04* | (2006.01) | |

(52) U.S. Cl.
CPC ............ *A61B 6/4476* (2013.01); *A61B 6/025* (2013.01); *A61B 6/035* (2013.01); *A61B 6/0457* (2013.01); *A61B 6/4429* (2013.01)

(58) Field of Classification Search
CPC ........ A61B 6/4429; A61B 6/547; A61B 6/588
See application file for complete search history.

(56) References Cited

U.S. PATENT DOCUMENTS

| | | | | |
|---|---|---|---|---|
| 5,023,899 A | * | 6/1991 | Ohlson .................. | A61B 6/022 378/177 |
| 5,185,777 A | * | 2/1993 | Hasegawa ............ | A61B 6/4283 250/580 |
| 5,734,694 A | | 3/1998 | Khutoryansky et al. | |
| 6,604,855 B2 | * | 8/2003 | Katoh ..................... | A61B 6/02 378/196 |
| 6,632,019 B2 | | 10/2003 | Katoh | |

* cited by examiner

*Primary Examiner* — Dani Fox
(74) *Attorney, Agent, or Firm* — WPAT, PC

(57) ABSTRACT

A scanning system for three-dimensional imaging comprises a bench, a gantry frame, a light source, a sensor and a control unit. The bench is to support a subject to be scanned. The gantry frame is movably mounted at a lateral side of the bench. The light source is movably mounted on the gantry frame so as to emit a light for a radiographic purpose. The sensor is movably mounted at a side of the bench, by opposing to the subject with respect to the bench, so as to receive the light emitted from the light source. The control unit is electrically coupled with the gantry frame, the light source and the sensor so as thereby to perform motion controls upon the gantry frame, the light source and the sensor.

19 Claims, 13 Drawing Sheets

SCANNING SYSTEM FOR THREE-DIMENSIONAL IMAGING

This application claims the benefit of Taiwan Patent Application Serial No. 103134914, filed Oct. 7, 2014 and U.S. Patent Application Ser. No. 61/894,979, filed Oct. 24, 2013 the subject matter of which is incorporated herein by reference.

BACKGROUND OF INVENTION

1. Field of the Invention

The invention relates to a scanning system for three-dimensional imaging, and more particularly to the scanning system of computed tomographic imaging that choose the most appropriate scan mode based on the characteristics of the subject to be scanned so as to obtain a corresponding optimal image by analyzing the transmitted projection data within a limited scan range.

2. Description of the Prior Art

Generally, conventional transmission imaging methods include the 2D plane radiography (such as an anteroposterior or a posteroanterior chest X-ray), the 3D computed tomography (CT), and so on. By having the X-ray imaging as an example, the 2D plane radiography can only provide a planar image without in-depth and clear information of individual organs. For instance, in a chest X-ray imaging, lesions at the cardiac area, mediastinum, diaphragm, spine and so on are not easy to be seen. On the other hand, though the CT can provide images of different depths, yet the cost is about ten times of the X-ray radiography and the radiation dose would be up to a hundred times of the X-ray radiography. Hence, the CT is hard to be the first-line diagnostic choice. According to the report No. 160 of the NCRP (National Council on Radiation Protection), the average yearly effective dose of the people in the United States is raised from 3.1 mSv in 1980 to 5.5 mSv in 2006. It is noted that the major reason responsive for such a hike is the increase of the radiation for medical examinations and therapies (from 0.5 mSv to 3.0 mSv), mainly from the CT. Thus, the issue of minimizing the risk and dose of the radiation without sacrificing medical image quality is one of the mainstream topics of the radiologic researches.

Besides the aforesaid 2D plane radiography and CT, one of recent developments is a limited-angle scan imaging method, called as the digital tomosynthesis. However, because only the projection information from limited-angle range can be provided, we believe that an appropriate scanning direction should be applied to different body portions. It is also understood that the spatial resolution of the tomosynthesis is directionally dependent, and the choice of the scanning direction therefor is sensitive and thus significant to the subject to be scanned. However, a conventional general purpose X-ray apparatus with the tomosynthesis function can perform the scanning only along a longitudinal direction. Definitely, such a uni-directional scanning pattern upon the subject to be scanned can't meet various demands anymore for a universal X-ray apparatus.

Generally, there are three types of radiographies: 2D radiography, dynamic fluoroscopic radiography, and computed tomography. For a general purpose X-ray apparatus, the first two types of radiographies are the basic, but the last one is optional. Recently, for the development in the digital image detector becomes mature, major manufacturers such as GE and Shimadzu have constructed the apparatus with the tomosynthesis functions. Contrary to the omni-angle scanning pattern of the conventional tomography, the new digital tomosynthesis can only capture the projection information within a limited range. For the direction of the scan trace can affect the imaging result, a current radiographic apparatus with the tomosynthesis function can only provide single-direction scanning, typically the longitudinal direction. Yet, it is understood that such a uni-directional scanning can't meet the demand of subjects with different characteristics to be scanned.

In U.S. Pat. No. 6,632,019, the radiographic apparatus has an X-ray tube device fixed to a pole and an X-ray image detecting portion facing the X-ray tube device to sandwich a top board therebetween so that fluoroscopying or radiographing can be carried out. It is noted that, while in scanning a lied-down subject, the X-ray tube as well as the X-ray image detecting portion are synchronously moved parallel with respect to the top board along an axial direction (i.e. the longitudinal direction of the top board). While the subject to be scanned in an upright position, the aforesaid X-ray tube device is individually evacuated toward a head or feet side of the subject, and a secondary X-ray tube device suspended from a ceiling comes in for performing fluoroscopic radiographing upon the subject in cooperation with the X-ray image detecting portion. In this disclosure, the support for the X-ray image detecting portion can be manually moved along, and only along, the longitudinal direction of the top board. No matter what position mode of the subject is, the apparatus of U.S. Pat. No. 6,632,019 provides only a longitudinal scan direction.

Further, in U.S. Pat. No. 5,734,694, another universal radiographic apparatus is disclosed. This radiographic apparatus allows an operator to select between a conventional radiographic mode and a linear tomographic mode. While in the conventional radiographic mode, an X-ray tube mounted to a tube crane positioned above an elevating table can be accurately controlled in longitudinal and vertical movement. Also, in the conventional radiographic mode, the apparatus may include following three operational patterns: (1) the table bucky automatically tracking motion of the tube crane, (2) the tube crane tracking vertical motion of the table so as to maintain a fixed SID, and (3) the tube crane tracking vertical movement of an associated wall bucky. While the audiographic apparatus is in the linear tomographic mode, the table bucky is moved laterally in opposition to movement of the tube crane, with angulation keeping the tube aimed at the bucky. It is noted that the scan direction of the linear tomographic mode is the longitudinal direction.

In the art, though the conventional CT apparatus can perform an omni-angle scanning to clearly present tomographic images of the subject to be scanned, yet the accompanying radiation dose of the CT testing is too high. Hence, the effort to reduce the CT radiation dose, including effort to reduce the unnecessary radiation testing, is definitely crucial to the medical industry. It is noted that performing scan within a limited range could also be a resort to reduce radiation dose. By trading off between the limited information of the limited-angle scanning and the image quality, the choice of a correct scanning direction for different body portions seems to be one of the most important considerations. Though the current general purpose X-ray apparatus is capable of performing tomosynthesis scanning, yet the scanning direction thereof is still limited to the longitudinal direction. Obviously, possible merits from scanning along an additional traverse or other direction and with a omni-angle scanning range are still in vain for the conventional general purpose X-ray apparatus.

SUMMARY OF THE INVENTION

Accordingly, it is the primary object of the present invention to provide a scanning system for three-dimensional imaging, capable of choosing an optimal scan mode based on the characteristics of the subject to be scanned and obtaining a corresponding optimal image by analyzing the transmitted projection data within a limited scan range.

In one embodiment of the present invention, the scanning system for three-dimensional imaging comprises a bench, a gantry frame, a light source, a sensor and a control unit. The bench is to support a subject to be scanned. The gantry frame is movably mounted at a lateral side of the bench. The light source is movably mounted on the gantry frame so as to emit a radiation beam, an array of radiation beams, an optical light beam or an array of optical light beams. The sensor is movably mounted at a side of the bench, by opposing to the subject to be scanned with respect to the bench, so as to receive the radiation beam or the optical light beam emitted from the light source. The control unit is electrically coupled with the gantry frame, the light source and the sensor so as thereby to perform motion control upon the gantry frame, the light source and the sensor.

All these objects are achieved by the scanning system for three-dimensional imaging described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a scanning system for three-dimensional imaging. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
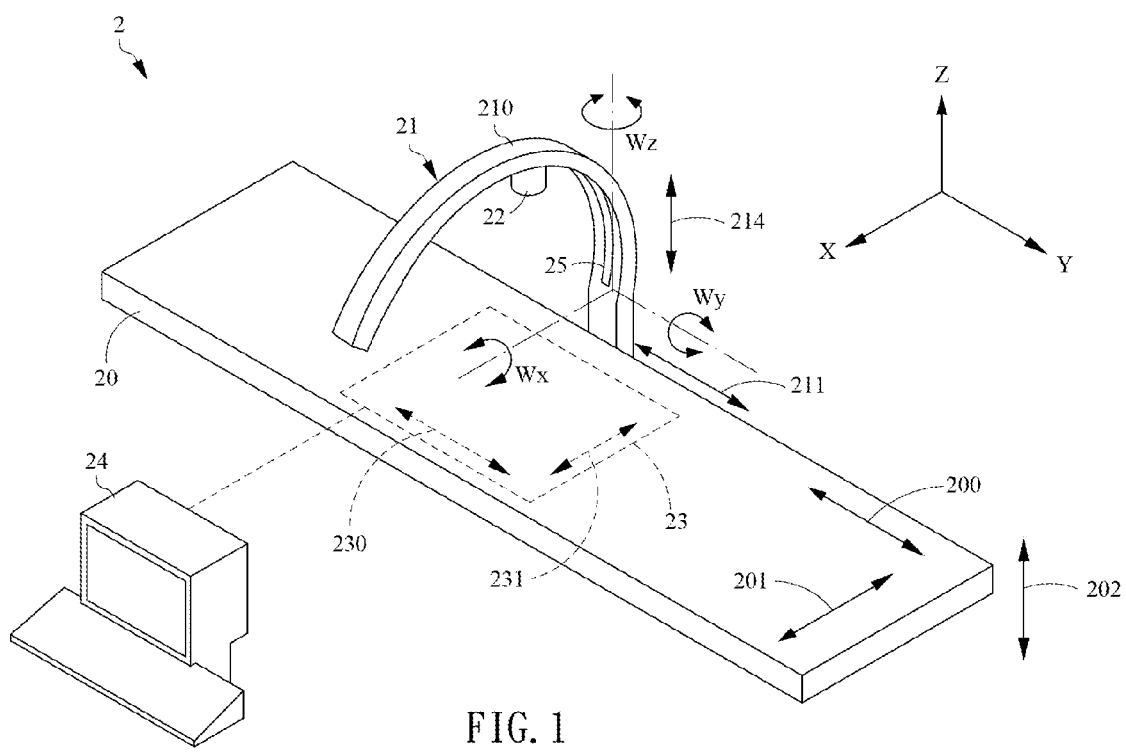
FIG. 1 is a schematic view of a first embodiment of the scanning system for three-dimensional imaging in accordance with the present invention.

Referring now to FIG. 1, a first embodiment of the scanning system for three-dimensional imaging in accordance with the present invention is schematically perspective shown. The scanning system for three-dimensional imaging 2 includes a bench 20, a gantry frame 21, a sensor 23 and a control unit 24. The gantry frame 21 has a light source 22, which is movably mounted on the gantry frame 21. In a operating mode of the scanning system, the bench 20 is to support thereon a subject to be scanned, in which the subject to be scanned can be a patient or an object per operator's need. The bench 20 can be a fixed platform electrically coupled with the control unit 24 via a driving assembly, such that the bench 20 can be driven to perform the first movement 200 along the Y axis of the XYZ orthogonal coordinate system shown in FIG. 1. in this XYZ coordinate system, every two of the X axis, the Y axis and the Z axis are perpendicular to each other. The driving assembly can be (but not limited to) a motor assembly, a screw bolt or a guide rail. In this first embodiment, the control unit 24 can be an apparatus that can perform signal processing and control functions, for example a computer, a programmable controller, or a combination of the former two. It is noted that the control unit 24 can provide a control interface for an operator to perform the related control, such as the control of the first movement 200 of the bench 20. In the present invention, the control interface can be a touch panel, a display and configuration interface, or an operator's input assembly such as the keyboard and the mouse.

In this first embodiment, the gantry frame 21, formed as an open-side arm over the bench 20, is located at a lateral side of the bench 20. Alternatives, in another embodiment not shown here, two gantry frames, each of which is formed as a single arm to extend over the platform 20, are located individually and respectively at opposing lateral sides of the platform 20. As shown in FIG. 1, the gantry frame 21 has a curve-shaped gantry frame 210 to extend upward and cross over the bench 20. The curve-shaped gantry frame 210 further includes thereon a curve-shaped guide rail 25. In this embodiment, the curve-shaped guide rail 25 electrically coupled with the control unit 24 can be (but not limited to) a curve-shaped guide motor. The light source 22 coupled to the curve-shaped guide rail 25 so as to be driven by the curve-shaped guide rail 25 to move along the curve-shaped gantry frame 210. In particular, the light source 22 can scan the subject to be scanned on the bench 20 along a traverse direction. In this embodiment, the traverse direction is the X-axial direction of FIG. 1. in addition, the curve-shaped guide rail 25 can be controlled by the control unit 24. The operator can operate user's operational interface in the control unit 24 so as to assure the moving destination of the light source 22.

The light source 22 electrically coupled with the control unit 24 is to allow the light source 22 to receive an operation command from the control unit 24 and then thereby to emit a radiation beam, a radiation beam array, an optical light beam or an optical light beam array to project onto the subject to be scanned on the bench 20. In this embodiment, the light source 22 can be a radiation source, such as an X-ray source from an X-ray tube or an X-ray tube array. Alternatively, the light source 22 can also be a y-ray source, a laser ray source or a laser ray array.

Figure 2A:
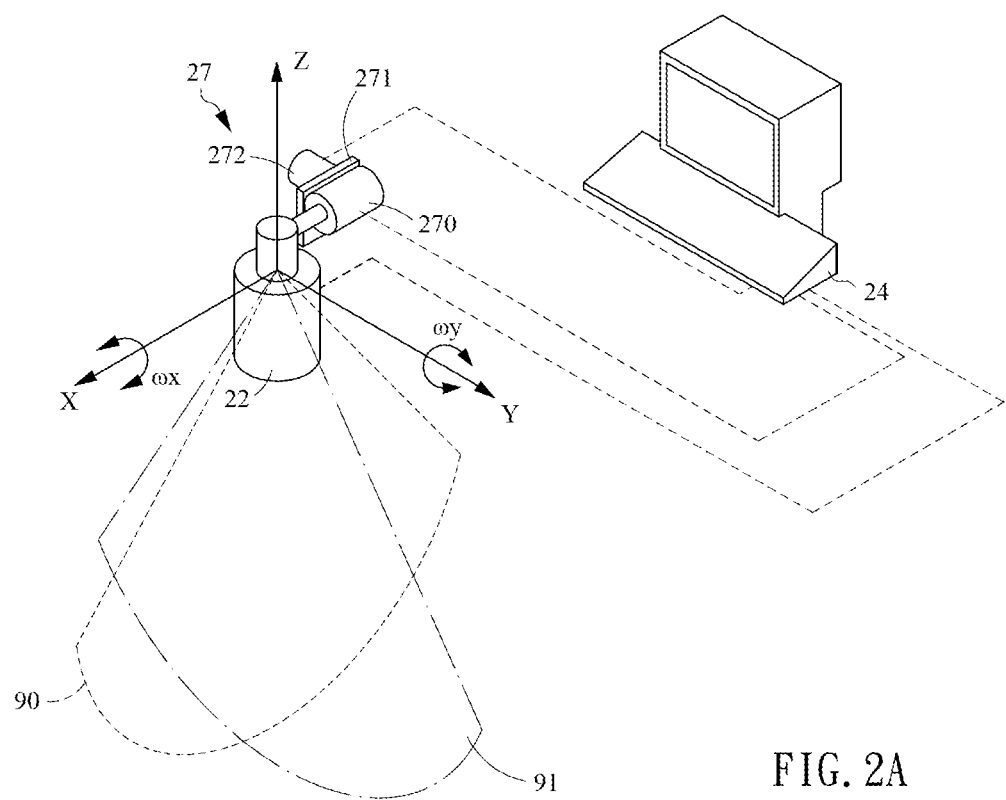
FIG. 2A demonstrates schematically rotations of the light source of FIG. 1.
Figure 2B:
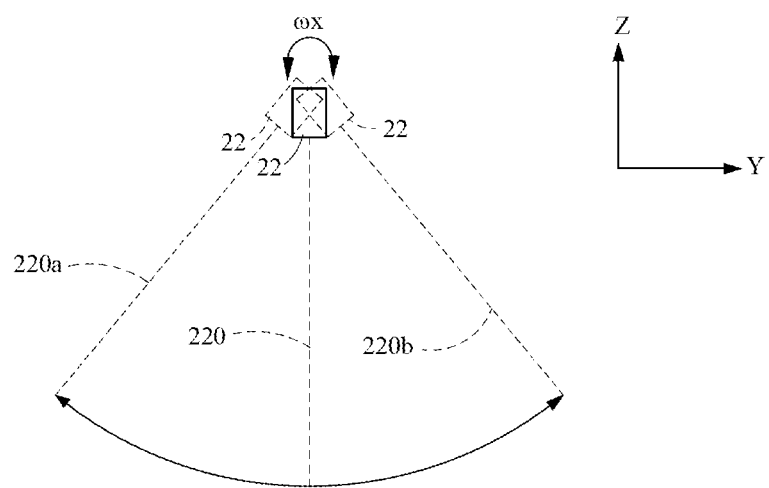
FIG. 2B shows schematically also rotations of the light source of FIG. 1, in a planar view.

Referring now to FIG. 2A and FIG. 2B, various rotations of the light source 22 of FIG. 1 are schematically demonstrated. The light source 22 coupled to a rotation-driving unit 27 can then perform a first rotation wx about the X axis or a second rotation wy about the Y axis, in both of which the light source 22 can only rotate within a limited angular range. In this embodiment, the rotation-driving unit 27, able to rotate about the X axis and the Y axis, has a first motor 270, a fixation plate 271 and a second motor 272. The first motor 270 coupled to the light source 22 is electrically coupled with the control unit 24. The fixation plate 271 is connected with the first motor 270. The second motor 272 connected with the fixation plate 271 is electrically coupled with the control unit 24. Further, the first motor 270 and the second motor 272 can be controlled by the control command of the control unit 24 so as to perform a responsive rotation. It is noted that the embodiment of the rotation-driving unit 27 in accordance with the present invention is not limited to that shown in FIG. 2A, but can be any appropriate device per design needs.

As shown in FIG. 2A, the first range 90 stands for the workable area of the first rotation ωx about a central axial line of the light source 22, while the second range 91 stands for the workable area of the second rotation ωy about a central axial line of the light source 22. Refer now to FIG. 2B, in which the central axial line of the light source 22 is the X axis, also in which the number 220, 220a and 220b indicate different rotation positions of the central axial line of the light source 22. The coordinate system demonstrated in either FIG. 2A or FIG. 2B is only typical and can be arbitrarily defined in accordance with user needs. For the light source 22 can move along the curve-shaped gantry frame 210 and can be driven to rotate, so the moving trace of the light source 22 would be one of curve-shaped moving traces, such that, in the testing, the radiation beam or the optical light beam can be emitted from various angles to project onto the subject to be scanned, penetrate the subject to be scanned as well as the bench 20, and finally reach the sensor. The data generated by the sensor then undergoes pre-processing, image reconstruction and post-processing so as to synthesize a corresponding tomosynthesis image for further interpretations by a technologist or a doctor.

Figure 3:
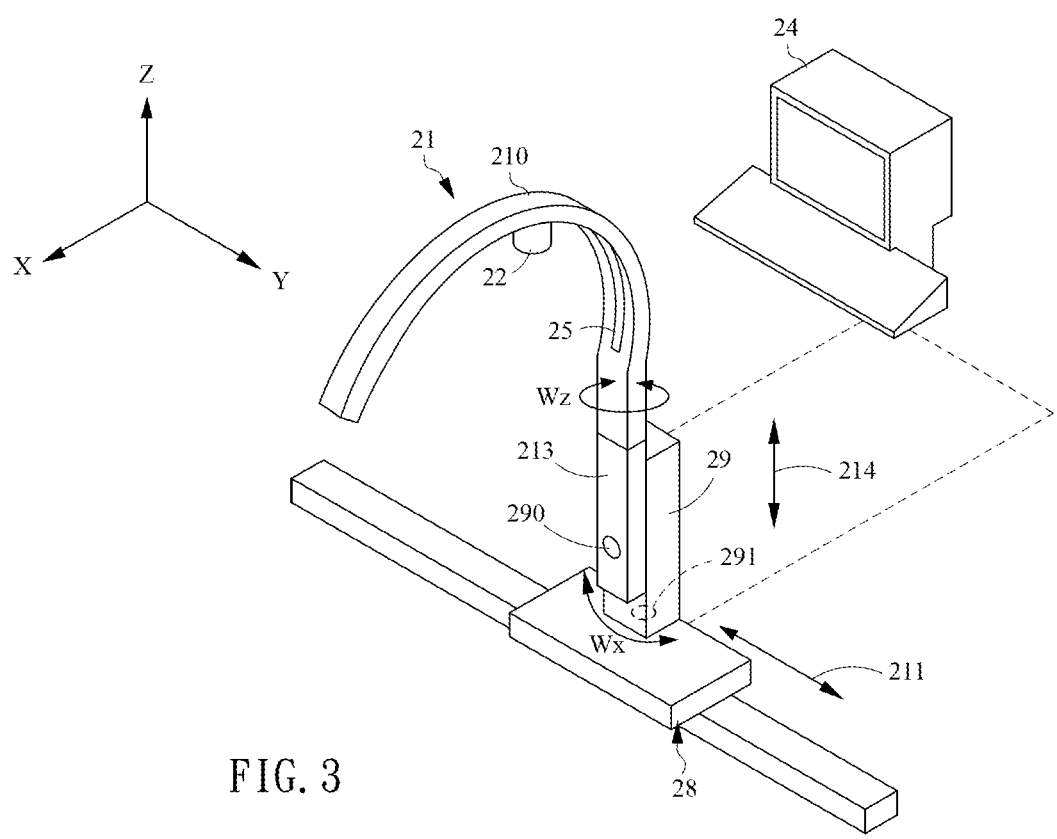
FIG. 3 is a schematic perspective view of the gantry frame of FIG. 1.

Referring now to FIG. 1 and FIG. 3, the driving assembly 28 electrically coupled with the control unit 24 can also be applied to drive the gantry frame 21 to undergo a linear motion, in which the gantry frame 21 performs the second movement 211 in the Y-axial direction. In the present invention, the driving assembly 28 can be any relevant device already in the marketplace, such as (but not limited to) a motor assembly, a screw bolt or a guide rail. Further, the first rotation-driving unit 29 electrically coupled with the control unit 24 can also be applied to drive the gantry frame 21 to undergo a third rotation Wx about the X axis. In this embodiment, the first rotation-driving unit 29 has an elevation-driving unit 290 to couple the motor onto the gantry frame 21, such that the gantry frame 21 can be controlled by the command of the control unit 24 to move up and down along the Z axis, i.e. the fourth movement 214 of the gantry frame 21 in the Z-axial direction. The first rotation-driving unit 29 further has a rotation-driving unit 291, also able to couple the motor onto the gantry frame 21, such that the gantry frame 21 can be controlled by the command of the control unit 24 to perform responsive rotation about the X axis. Though FIG. 3 demonstrates a single first rotation-driving unit 29 for rotating the gantry frame 21 about the X axis, yet it shall be understood to the art that another rotation-driving unit can exist to rotate the gantry frame 21 about the Y axis (i.e. the fourth rotation Wy) or about the Z axis (i.e. the fifth rotation Wz). In particular, the gantry frame 21 can have a lower gantry frame 213 rotationally coupled with the curve-shaped gantry frame 210. In addition, the lower gantry frame 213 can further include a driving unit (a motor for example) to be controlled by a command of the control unit 24 to provide a response of rotational power to rotate the curve-shaped gantry frame 210 to a desired position about the Z axis. It is noted that the operator can reach the user's operational interface of the control unit 24 to control the rotation angle and the movement destination of the gantry frame 21.

Referring back to FIG. 1, the sensor 23 is mounted to the side (bottom side) of the bench 20 by opposing to the side thereof (upper side) supporting the subject to be scanned. The sensor 23 receives the radiation beam from the light source 22 and then generates a corresponding signal. The signal is forwarded to the control unit 24 for constructing a projection image. Then, after the image undergoes pre-processing and image reconstruction, a tomographic image can be synthesized (tomosynthesis image) and can be displayed on a display screen of the control unit 24. In this embodiment, the sensor 23 can be driven to perform a third movement 230 in the Y-axial direction and a fifth movement 231 in the X-axial direction. The first movement 200 of the bench 20, the third movement 230 of the sensor 23 and the second movement 211 of the gantry frame 21 can be performed independently or synchronously by the control unit 24. The command of the control unit 24 can be inputted manually from user's operational interface, and also can be generated automatically by a preset program of the control unit 24.

Figure 4A:
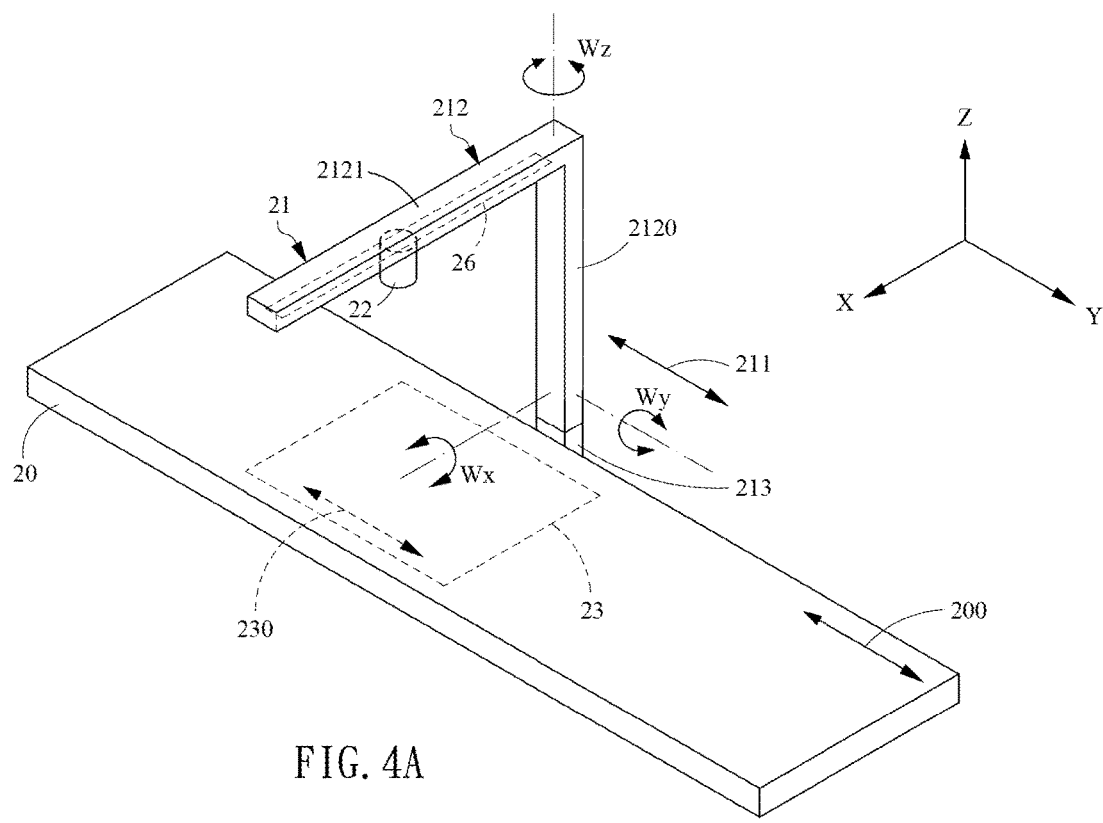
FIG. 4A is a schematic view of a second embodiment of the scanning system for three-dimensional imaging in accordance with the present invention.

Referring now to FIG. 4A, a second embodiment of the scanning system for three-dimensional imaging in accordance with the present invention is schematically shown. In this embodiment, the bench 20, the light source 22 and the sensor 23 are exactly the same as those in the first embodiment. The major difference in between is that the gantry frame 21 of this embodiment has an L-shaped gantry frame 212 located at one side of the bench 20 to perform a linear first movement 200 in the Y-axial direction. The L-shaped gantry frame 212 further includes a first gantry frame 2120 and a second gantry frame 2121, in which the second gantry frame 2121 connecting perpendicular to the first gantry frame 2120 so as to form the L-shaped gantry frame 212. Similar to the embodiment shown in FIG. 3, the first gantry frame 2120 is coupled with the driving assembly 28 and the first rotation-driving unit 29, such that the gantry frame 21 can undergo a second movement 211 in the Y-axial direction and a rotation about the X axis. Further, the L-shaped gantry frame 212 can also undergo the aforesaid fourth rotation Wy and fifth rotation Wz.

In this embodiment, the second gantry frame 2121 is a linear gantry frame to cross the bench 20 in the X-axial direction. The second gantry frame 2121 further includes a linear motion unit 26, such as a linear motor, a regular motor, a screw bolt, a guide rail, or a combination thereof. The linear motion unit 26 coupled with the light source 22 can drive the light source 22 to move on the second gantry frame 2121 in the X-axial direction so as to scan the subject to be scanned on the bench 20 in a traverse manner.

Further, in the second embodiment, the second gantry frame 2121 connects the first gantry frame 2120 so as to form the L-shaped gantry frame 212. In another embodiment, two first gantry frames 2120 can be constructed individually to both sides of the bench 20, and can integrate the middle second gantry frame 2121 so as to form a ⊓-shaped gantry frame, in which the second gantry frame 2121 crosses traverse the bench 20 in the X-axial direction.

Figure 4B:
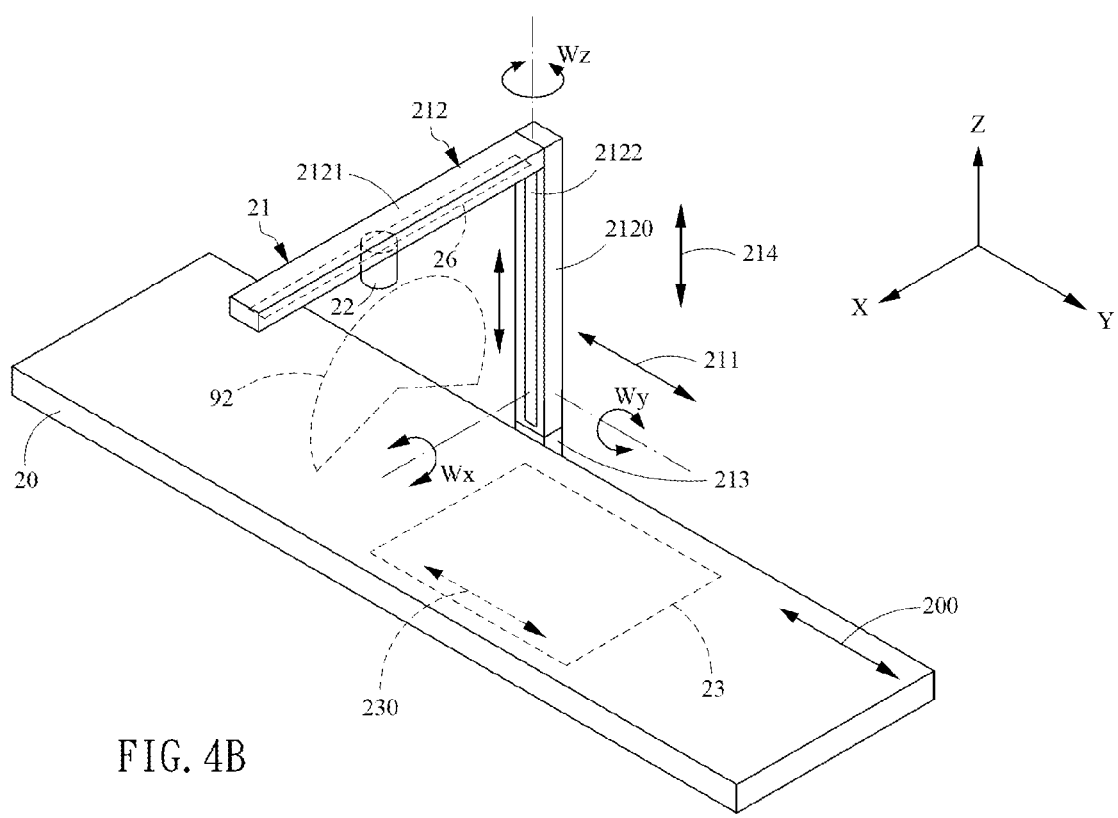
FIG. 4B is a schematic view of a third embodiment of the scanning system for three-dimensional imaging in accordance with the present invention.

Referring now to FIG. 4B, a third embodiment of the scanning system for three-dimensional imaging in accordance with the present invention is schematically shown. In this embodiment, by having the light source 22 to move in the X-axial direction and synchronously the first gantry frame 2120 to move up and down in the Z-axial direction (i.e. the fourth movement 214), the moving trace of the radiation beam on the XZ plane would form a curve-shaped moving trace (the curve 92 as shown). By having the light source 22 to undergo a curve-shaped movement about the sensor 23 and synchronously the aforesaid rotation, the distance from the emitting point of the light source 22 to the center of the sensor 23 would stay the same during the operation. In this embodiment, the linear motion unit 26 can drive the light source 22 to move on the second gantry frame 2121 in the X-axial direction, and another linear motion unit on the first gantry frame 2120 can be applied to further control the second gantry frame 2121 to move along a guide rail 2122 in the Z-axial direction, in which the guide rail 2122 is located at the first gantry frame 2120. In addition, by applying the rotation-driving unit 27 of FIG. 2A, the light source 22 can be controlled to rotate about the Y axis. With the rotations about the X axis and the Z axis, the light source 22 can be moved to a desired position. With the rotation about the Y axis, the emission angle of the light source 22 can then be adjusted. In FIG. 4B, curve 92 stands for the moving trace of the light source 22. Through the control of the moving trace, various projection angles of the light source 22 can be achieved to project the subject to be scanned or the patient, such that the imaging data can be provided to the medical technologist or the doctor for further interpretations.

Figure 4C:
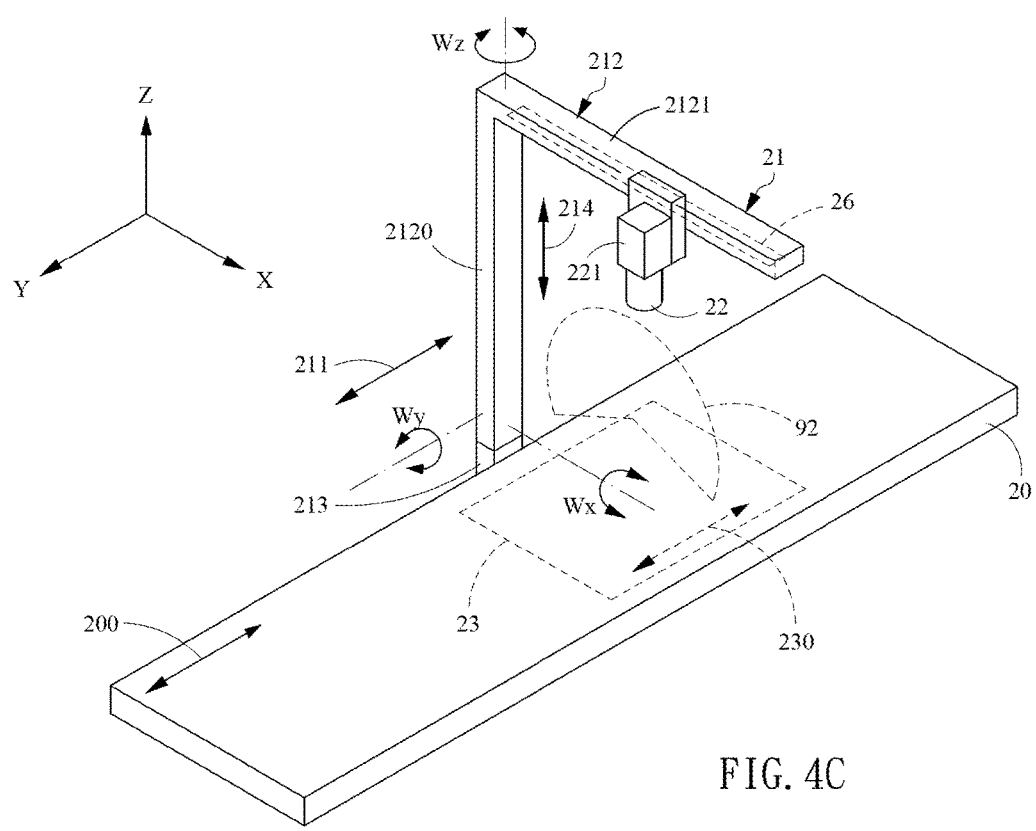
FIG. 4C is a schematic view of a fourth embodiment of the scanning system for three-dimensional imaging in accordance with the present invention.

Referring to FIG. 4C, a fourth embodiment of the scanning system for three-dimensional imaging in accordance with the present invention is schematically shown. In this embodiment, the light source 22 is coupled with a linear motion device 221. Through the movement of the light source 22 in the X-axial direction and synchronously the up-and-down fourth movement 214 of the light source 22 in the Z-axial direction driven by the linear motion device 221, the moving trace of the radiation beam on the XZ plane would form a curve-shaped moving trace (i.e. curve 92 as shown). Namely, by applying this embodiment, the same result as that shown in FIG. 4B can be obtained. In this embodiment, the linear motion unit 26 can be applied to drive the light source 22 to move on the second gantry frame 2121 in the X-axial direction, and also the linear motion device 221 can be applied to control the moving of the light source 22 in the Z-axial direction. In addition, the rotation-driving unit 27 of FIG. 2A can be applied to control the rotation of the light source 22 about the Y axis. With the rotations about the X axis and the Z axis, the light source 22 can be moved to the desired position. With the rotation about the Y axis, the radiation angle of the light source 22 can be adjusted. In FIG. 4C, the curve 92 stands for the moving trace of the light source 22. By controlling the formation of the moving trace, the light source 22 can project the subject to be scanned or the patient at various angles, so that sufficient data can be provided to the medical technologist and the doctor for further interpretations.

Figure 4D:
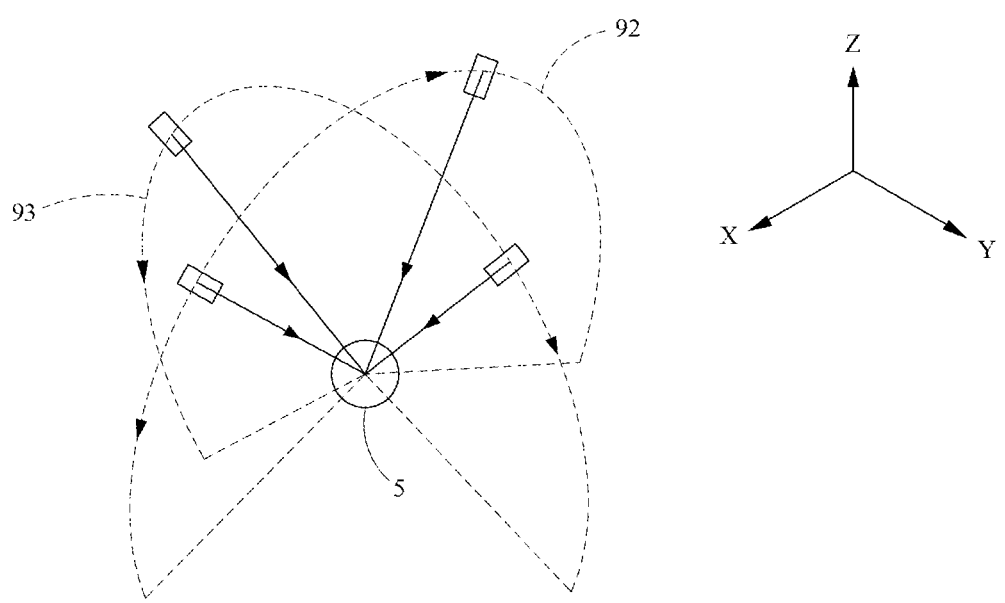
FIG. 4D shows schematically various moving traces of the light source for an embodiment in accordance with the present invention.

In addition, refer now to FIG. 4D for various embodiments of the moving trace of the light source in accordance with the present invention. As shown, by having the light source 22 to move in both the Y-axial direction and the Z-axial direction and to rotate about the X axis, a moving trace 93 can be formed on the YZ plane, by which the radiation beams with various radiation angles can be projected onto the subject to be scanned 5. In this embodiment, a driving assembly, resembled to the driving assembly 28 of FIG. 3, can be applied to move the light source 22 in the Y-axial direction. Also, a linear motion unit mounted on the first gantry frame 2120 is to simultaneously drive the L-shaped gantry frame 212 to move in the Z-axial direction and drive the second gantry frame 2121 to move on the first gantry frame 2120, while the light source 22 displaces. By providing the rotation-driving unit such as the rotation-driving unit 27 of FIG. 2A, the light source 22 can then rotate about the X axis. With the movements in the Y-axial direction and the Z-axial direction, the light source 22 can be displaced to a desired location. By having the rotation about the X axis, the radiation angle of the light source 22 can then be adjusted.

Figure 4E:
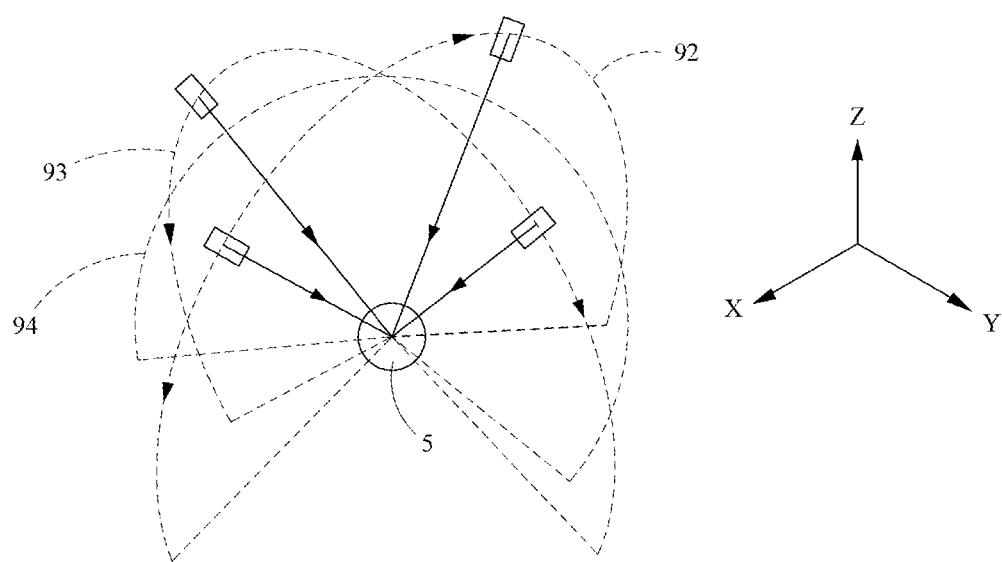
FIG. 4E shows schematically various moving traces of the light source for another embodiment in accordance with the present invention.

Besides of the moving traces shown in FIG. 4B and FIG. 4D, please also refer to FIG. 4E. As shown, the moving trace can also locate on an oblique plane with respect to the XZ plane or the YZ plane. To form such a specific moving trace 94, one method is to rotate the L-shaped gantry frame 212 of FIG. 4B, and another method is to rotate the curve-shaped gantry frame 210 of FIG. 1 about the Z axis by a specific angle when the light source 22 follows the moving trace of FIG. 4B. Thereupon, versatility in radiation angle can then be achieved.

Further, in the embodiments from FIG. 1 through FIG. 4C, a driving assembly electrically coupled with the control unit 24 and the bench 20 can be applied to drive the bench 20 to undergo the sixth movement 201 in the X-axial direction and the seventh movement 202 in the Z-axial direction with respect to the coordinate system of FIG. 1.

Figure 5A:
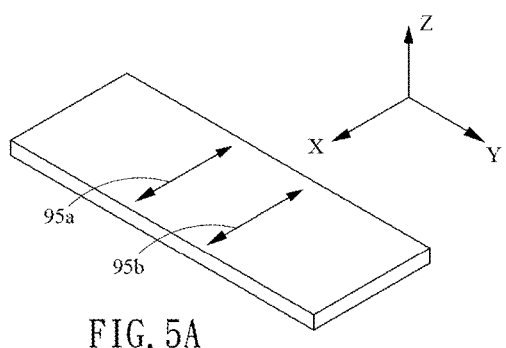
FIG. 5A shows schematically an embodiment of linear moving traces of the light source in accordance with the present invention.
Figure 5C:
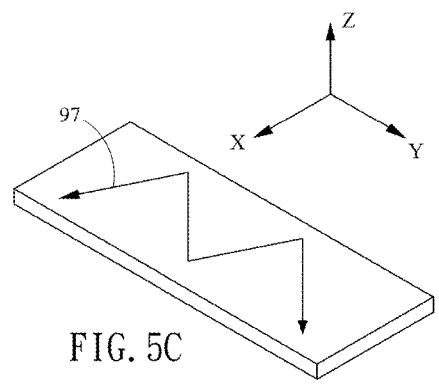
FIG. 5C shows schematically a further embodiment of linear moving traces of the light source in accordance with the present invention.
Figure 5B:
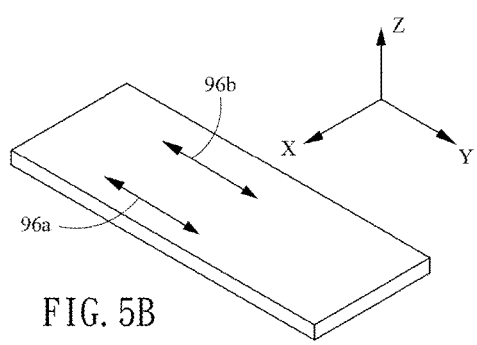
FIG. 5B shows schematically another embodiment of linear moving traces of the light source in accordance with the present invention.

Referring now to FIG. 5A to FIG. 5C, various embodiments of linear moving traces of the light source in accordance with the present invention are respectively shown. In FIG. 5A, the linear moving trace of the light source 22 can be formed by moving the light source 22 along the curve-shaped gantry frame 210 of FIG. 1, or by moving the second gantry frame 2121 along the X axis in any of FIG. 4A to FIG. 4C. The first moving trace 95a and the second moving trace 95b stand for different locations of the gantry frame 21 in the Y axis. In FIG. 5B, the linear moving trace of the light source 22 can be formed by moving the curve-shaped gantry frame 210 of FIG. 1 or the L-shaped gantry frame 212 of any of FIG. 4A to FIG. 4C in the Y-axial direction, such that the moving trace along the Y axis can be formed. As shown, the third moving trace 96a and the fourth moving trace 96b stand for different locations of the light source 22 in the X axis on the curve-shaped gantry frame or the L-shaped gantry frame. In FIG. 5C, the zig-zag moving trace 97 of the light source 22 in either of FIG. 1 and FIG. 4A through FIG. 4C can be formed by moving the light source 22 on the curve-shaped gantry frame 210 or the L-shaped gantry frame 212 and integrally by moving the gantry frame 21 along the Y axis. It is noted that, while the light source 22 is controlled to follow the zig-zag moving trace 97, versatility of detection area can be enhanced, examination convenience for the medical technologist or doctor can be provided, and the time required for the radiographic examinations can be substantially reduced.

Figure 6A:
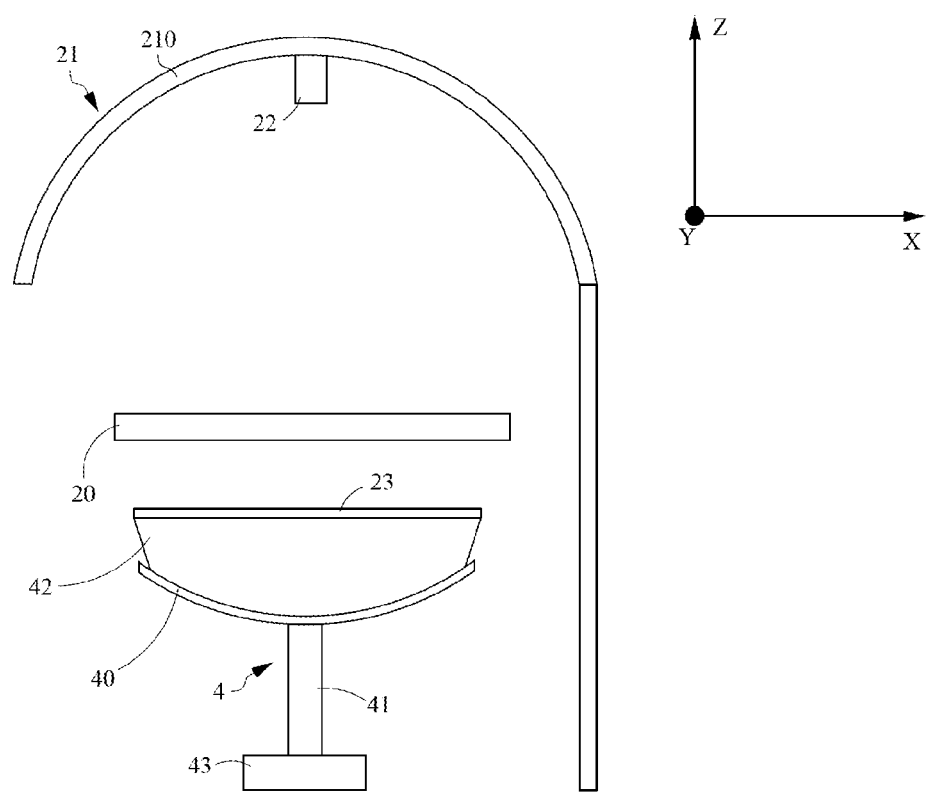
FIG. 6A shows an extended embodiment of FIG. 1, in which the sensor of the extended embodiment can rotate about a specific axis.

Referring now to FIG. 6A, an extended third embodiment of the scanning system for three-dimensional imaging in accordance with the present invention is schematically shown. Typically, the scanning system for three-dimensional imaging of this extended embodiment is resembled to that of FIG. 1. The major difference in between is that the sensor of this extended embodiment can rotate about a specific axis. In this embodiment, the specific axis is the Y axis, and the sensor 23 can also undergo a linear motion in the Y-axial direction. The sensor 23 is supported by a supportive assembly 4, and the supportive assembly 4 includes a second rotation-driving unit 40, a supportive frame 41, a sensor support 42 and a guide rail 43, in which the sensor 23 is mainly supported by the sensor support 42 and the second rotation-driving unit 40 is to rotate the sensor support 42 and the sensor 23. One end of the supportive frame 41 is connected to the second rotation-driving unit 40, while another end thereof is slippery connected with the guide rail 43. The guide rail 43 can drive the supportive frame 41 to move in the Y-axial direction so as to change the location of the sensor 23 on the Y axis.

Figure 6B:
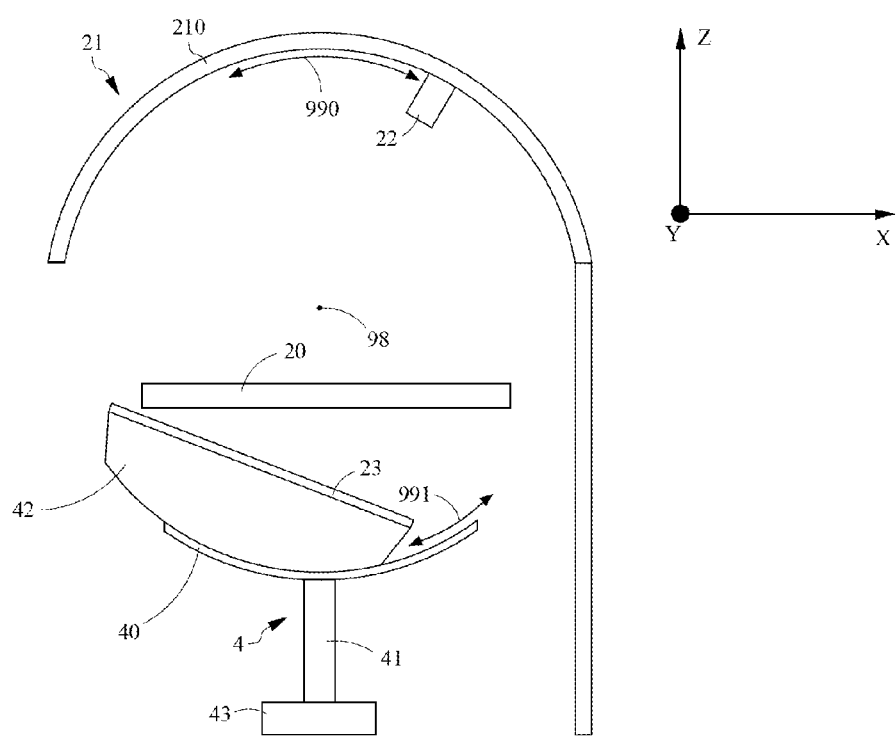
FIG. 6B is another state of FIG. 6A.
Figure 6C:
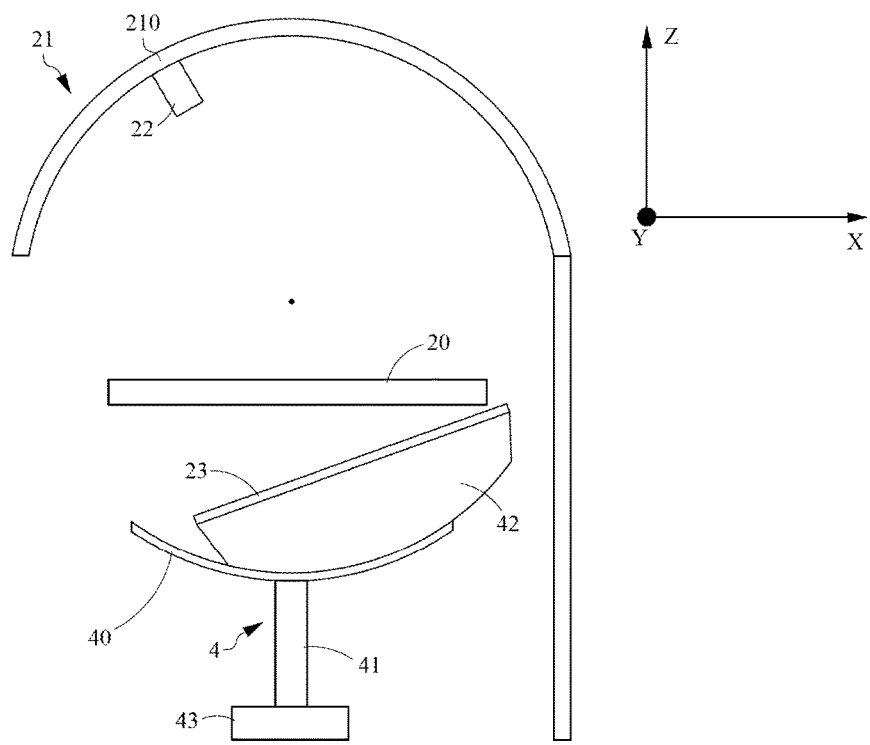
FIG. 6C is a further state of FIG. 6A.

Referring now to FIG. 6B and FIG. 6C, two rotational states of the sensor 23 driven by the supportive assembly 4 are shown. for the light source 22 able to move on the curve-shaped gantry frame 210 and to rotate with a specific angle to project the radiation beam onto the subject to be scanned, the sensor 23 of this embodiment is to be adjusted in coherence angularly with the light source 22, such that the radiation beam penetrating the subject to be scanned can be received by the sensor 23 under the subject to be scanned. Particular, in FIG. 6B, the second rotation-driving unit 40 rotates the sensor support 42 in a clockwise direction so as to vary the facing angle of the sensor 23 to a direction coherent to the locations of the light source 22. Further, in FIG. 6C, the second rotation-driving unit 40 rotates the sensor support 42 in a counter clockwise direction so as to vary the facing angle of the sensor 23 for corresponding to the angling of the light source 22. Though the supportive assembly 4 of FIG. 6A is to pair the curve-shaped gantry frame 210 of FIG. 1, yet it is noted that the supportive assembly 4 can also match the L-shaped gantry frame 212 of FIG. 4A or the aforesaid ⊓-shaped gantry frame. As shown in FIG. 6B, for the sensor 23 and the light source 22 can be driven to rotate around the common axis 98 so as to form the first curve-shaped movement 990 and the second curve-shaped movement 991 respectively on the gantry frame 21 and the sensor support 42. Therefore, while in examining different body portions of the subject to be scanned, the distance between the sensor 23 and the light source 22 can be adequately adjusted so as to meet the instant requirement for imaging.

By providing the present invention, at least two manifolds of applicable advantages can be obtained as follows.

(1) According to existing experimental data, it has been proved that different scanning directions would significantly affect the distribution of the spatial resolution of the tomosynthesis (synthesized tomographic) image. Hence, multi-dimensional movements and rotations of the gantry frame and the light source provided by the present invention make possible to have the light source moving in the X-axial direction, in the Y-axial direction, or along a zig-zag moving trace formed by integrating synchronously motions in X and Y directions so as to examine the subject to be scanned in a more precise and effective way. Also, the sensor of the present invention can perform a curve-shaped movement. Thus, the present invention can be applied to the two-dimensional planar radiography, the three-dimensional tomosynthesis imaging and the three-dimensional cone-beam computed tomography. It is believed that choosing the scan pattern upon characteristics of the subject to be tested and scanning in a less angular manner in accordance with the present invention can help obtain an optimal image. Contrary to the omni-angle CT, for a limited-angle scan range is applied in this present invention for scanning the subject to be scanned, the radiation dose received by the subject to be scanned can be reduced and the examination time can be greatly reduced as well. Therefore, the present invention can be applied effectively and safely to most of the radiographic imaging, particularly in bio-medical field and in the non-destruction testing industry.

(2) By compared to the conventional computed tomography (CT), the sensor of the present invention is located at a side opposing to the light source, and is rotated coaxially with the light source so as to gather information for image reconstruction. For the sensor and the light source can be individually driven to rotate about a common axis so as to perform corresponding curved movement on the gantry frame and the sensor support, respectively, so while in examining different portions of the subject to be scanned, the distance between the sensor and the light source can be adequately adjusted to acquire an optimal magnification. In addition, the present invention can perform the two-dimensional planar radiography, the three-dimensional tomosynthesis imaging and the three-dimensional cone-beam computed tomography, and can be applied to the radiation medical imaging field, the veterinary radiation imaging field, the industrial nondestructive testing field, etc.

While the present invention has been particularly shown and described with reference to a preferred embodiment, it will be understood by those skilled in the art that various changes in form and detail may be without departing from the spirit and scope of the present invention.

What is claimed is:

1. A scanning system for three-dimensional imaging, comprising:
    a bench for supporting thereon a subject to be scanned;
    a gantry frame, movably mounted on a lateral side of the bench;
    a light source, movably mounted on the gantry frame, for emitting one of a group comprising a radiation beam, a radiation beam array, an optical light beam and an optical light beam array;
    a sensor, movably mounted on the bench for receiving the beam emitted by the light source; and
    a control unit, electrically coupled with the gantry frame, the light source and the sensor, for controlling movements of the gantry frame, the light source, and the sensor,
    wherein the control unit is electrically coupled with a first rotation-driving unit for driving the gantry frame to perform a third rotation about an X axis;
    wherein the control unit is further electrically coupled with at least another first rotation-driving unit for driving the gantry frame to perform a fourth rotation about a Y axis and a fifth rotation about a Z axis, in which the X axis, the Y axis and the Z axis are mutually perpendicular to each other.

2. The scanning system for three-dimensional imaging of claim 1, wherein the light source is connected to a rotatable unit, the rotatable unit driving the light source within a limited angular range to perform a first rotation about an X axis and a second rotation about a Y axis, in which the X axis is perpendicular to the Y axis.

3. The scanning system for three-dimensional imaging of claim 2, wherein the rotatable unit further includes:
a first motor, for driving the light source to rotate about a X axis and electrically coupled with the control unit;
a second motor, for driving the light source to rotate about a Y axis and electrically coupled with the control unit, the first motor and the second motor being controlled by the control unit to perform responsive rotations.

4. The scanning system for three-dimensional imaging of claim 1, wherein the control unit is electrically coupled with a driving assembly for driving the gantry frame to undergo a linear motion.

5. The scanning system for three-dimensional imaging of claim 1, wherein the control unit drives the light source to move along the X axial, and the control unit drives the gantry frame to move along a Z axis, such that a curve-shaped moving trace is formed to the light source, in which the X axis, the Y axis and the Z axis are mutually perpendicular to each other.

6. The scanning system for three-dimensional imaging of claim 5, wherein, while the light source follows the curve-shaped moving trace, a rotation of the light source is introduced to fix a distance between an emission point of the light source and a center of the sensor.

7. The scanning system for three-dimensional imaging of claim 1, wherein a linear stage is connected with the light source, and a curve-shaped moving trace is formed to the light source by having the linear stage to drive the light source to move along a Z axis and simultaneously by having the control unit to drive the light source to move on the gantry frame along the X axis, in which the X axis, the Y axis and the Z axis are mutually perpendicular to each other.

8. The scanning system for three-dimensional imaging of claim 1, wherein the control unit drives the sensor to perform a linear motion along one of an X axis and a Y axis.

9. The scanning system for three-dimensional imaging of claim 1, wherein the bench is movable and electrically coupled with the control unit for controlling the bench to perform a linear motion along a Z axis.

10. The scanning system for three-dimensional imaging of claim 1, wherein the gantry frame is a curve-shaped gantry frame extended to cross the bench along an X axis.

11. The scanning system for three-dimensional imaging of claim 10, wherein the curve-shaped gantry frame further includes a curve-shaped guide rail electrically coupled with the control unit, the light source connected with the curve-shaped guide rail, the light source being driven by the curve-shaped guide rail to move along the curve-shaped gantry frame.

12. The scanning system for three-dimensional imaging of claim 1, wherein the gantry frame has an L-shaped gantry frame to undergo a linear motion along a Y axis.

13. The scanning system for three-dimensional imaging of claim 12, wherein the L-shaped gantry frame includes a first gantry frame and a second gantry frame connected with the first gantry frame, the second gantry frame formed as a linear frame to cross the bench along an X axis, in which the X axis is perpendicular to the Y axis.

14. The scanning system for three-dimensional imaging of claim 13, wherein the second gantry frame further includes a linear motion unit connected with the light source for driving the light source to move on the second gantry frame along an X axis, in which the X axis is perpendicular to the Y axis.

15. The scanning system for three-dimensional imaging of claim 13, wherein the first gantry frame has a guide rail and a linear motion unit, the linear motion unit controlling the second gantry frame to move on the guide rail along a Z axis, in which the Z axis is perpendicular to the Y axis.

16. The scanning system for three-dimensional imaging of claim 13, wherein two first gantry frames formed at two respective opposing ends of the second gantry frame thereof, the two first gantry frames being located respectively to two opposing lateral sides of the bench, the second gantry frame being across over the bench along an X axis.

17. The scanning system for three-dimensional imaging of claim 1, further including a supportive assembly, wherein the supportive assembly further includes:
a second rotation-driving unit;
a supportive frame, having one end thereof connected with the second rotation-driving unit;
a sensor support for supporting the sensor, the second rotation-driving unit being to rotate the sensor support and the sensor; and
a guide rail, slippery connected with another end of the supportive frame that is opposite to the end connecting the second rotation-driving unit.

18. The scanning system for three-dimensional imaging of claim 17, wherein the guide rail drives the supportive frame to move along a Y axis so as thereby to displace the sensor on the Y axis.

19. The scanning system for three-dimensional imaging of claim 1, wherein the control unit drives the light source to move on the gantry frame, and simultaneously the gantry frame moves along a Y axis, such that a zig-zag moving trace is formed.

* * * * *